(12) United States Patent
Escobar Fuertes

(10) Patent No.: US 10,610,322 B2
(45) Date of Patent: Apr. 7, 2020

(54) CARTRIDGE FOR MEDICAL AND HOSPITAL WASTE

(71) Applicant: Adrian Escobar Fuertes, Barcelona (ES)

(72) Inventor: Adrian Escobar Fuertes, Barcelona (ES)

( * ) Notice: Subject to any disclaimer, the term of this patent is extended or adjusted under 35 U.S.C. 154(b) by 73 days.

(21) Appl. No.: 15/571,867

(22) PCT Filed: May 4, 2016

(86) PCT No.: PCT/ES2016/070343
§ 371 (c)(1),
(2) Date: Nov. 6, 2017

(87) PCT Pub. No.: WO2016/177927
PCT Pub. Date: Nov. 10, 2016

(65) Prior Publication Data
US 2018/0296298 A1 Oct. 18, 2018

(30) Foreign Application Priority Data

May 7, 2015 (ES) ................................ 201530528 U
May 18, 2015 (ES) ................................ 201530579 U

(51) Int. Cl.
*A61L 11/00* (2006.01)
*A61B 50/36* (2016.01)
(Continued)

(52) U.S. Cl.
CPC ........ *A61B 50/362* (2016.02); *B02C 19/0075* (2013.01); *B09B 3/0075* (2013.01);
(Continued)

(58) Field of Classification Search
CPC ....... A61B 50/362; A61B 50/30; A61B 50/36; A61B 2050/3008; A61L 11/00; B02C 19/0075; B09B 3/0075; B65D 5/48044; B65D 5/48042; B65D 5/48046; B65D 5/48048; B65D 5/5002; B65D 5/327; B65D 5/3621; B65D 5/0209; B65D 5/4804;
(Continued)

(56) References Cited

U.S. PATENT DOCUMENTS 1,184,956 A * 5/1916 Hoppke ............... B65D 5/2047
229/104
1,902,072 A * 3/1933 Harrod ..................... B65D 3/00
229/117.01
(Continued)

FOREIGN PATENT DOCUMENTS

WO 2012/056082 A1 5/2012

*Primary Examiner* — Gideon R Weinerth
(74) *Attorney, Agent, or Firm* — Hoglund & Pamias, PSC; Roberto J. Rios

(57) ABSTRACT

Disclosed is a cartridge for medical and hospital waste, which comprises: a tubular body (1) provided with a base (3) and which is folded flat along the centre of the base (3) and along folding lines (12) on the tubular body, forming a flat body that can be stored easily; and a grid (2) made of sheets of card, which is disposed folded inside the tubular body (1) and which, when the cartridge is unfolded, opens to occupy the entire inside surface of the cartridge, defining cavities for receiving the medical waste. The base (3) can be formed from stiff card.

6 Claims, 2 Drawing Sheets

(51) Int. Cl.
*B09B 3/00* (2006.01)
*B02C 19/00* (2006.01)
*B65D 37/00* (2006.01)
*B65D 5/36* (2006.01)
*B65D 5/496* (2006.01)
*B65D 5/02* (2006.01)

(52) U.S. Cl.
CPC .............. *A61B 50/36* (2016.02); *A61L 11/00* (2013.01); *B65D 5/0209* (2013.01); *B65D 5/3614* (2013.01); *B65D 5/4804* (2013.01); *B65D 37/00* (2013.01)

(58) Field of Classification Search
CPC .......... B65D 25/04; B65D 37/00; B65D 3/06; B65D 3/10; B65D 3/12; B65D 3/14; B65D 3/16; B65D 3/18; B65D 3/20; B65D 5/3614; B65D 5/00; A61M 5/3205; B31D 5/0004
USPC ..... 220/507; 229/104, 5.5, 117.06, 4.5, 183; 206/365, 366
See application file for complete search history.

(56) References Cited

U.S. PATENT DOCUMENTS

| | | | | |
|---|---|---|---|---|
| 3,101,652 A * | 8/1963 | Imielinski | .......... | B65D 5/48026 229/120.31 |
| 3,628,718 A * | 12/1971 | Broyles | .................. | B65D 5/324 220/560.15 |
| 3,843,039 A * | 10/1974 | Brown | ............... | B65D 5/48026 229/120.31 |
| 4,109,848 A * | 8/1978 | Kipp | ........................ | B65D 3/02 229/104 |
| 4,375,849 A * | 3/1983 | Hanifl | ................. | A61M 5/3205 206/366 |
| 4,418,861 A * | 12/1983 | McFarland | .......... | B65D 77/062 229/108.1 |
| 4,869,366 A * | 9/1989 | Bruno | ................. | A61M 5/3205 206/370 |
| 5,038,929 A * | 8/1991 | Kubofcik | ............ | A61M 5/3205 206/210 |
| 5,152,394 A * | 10/1992 | Hughes | ................. | A61M 5/002 206/366 |
| 5,171,114 A * | 12/1992 | Dunn | ........................ | B60P 7/16 206/593 |
| 5,230,426 A * | 7/1993 | Keefe | ................. | A61M 5/3205 206/205 |
| 5,265,724 A * | 11/1993 | Dondlinger | ......... | A61M 5/3205 206/365 |
| 5,291,997 A * | 3/1994 | He | ........................ | A61M 5/002 206/366 |
| 5,325,965 A * | 7/1994 | Kelley | ................ | A61M 5/3205 206/366 |
| 5,445,315 A * | 8/1995 | Shelby | ................. | B65D 5/3628 220/592.17 |
| 5,524,634 A * | 6/1996 | Turkel | ............... | A61B 10/0096 600/562 |
| 5,575,385 A * | 11/1996 | Zona | .................... | B31D 3/0284 206/256 |
| 6,152,359 A * | 11/2000 | Clark | ................... | B65D 5/0209 229/104 |
| 6,196,449 B1 * | 3/2001 | Chen | .................... | B65D 5/4804 229/120.26 |
| 6,290,091 B1 * | 9/2001 | Bell | .................... | B65D 81/3876 220/739 |
| 6,513,704 B1 * | 2/2003 | Perot | .................. | B65D 5/0209 229/104 |
| 7,328,833 B1 * | 2/2008 | Wiley | ..................... | B65D 5/32 229/108.1 |
| 8,485,357 B2 * | 7/2013 | Song | ..................... | A61M 5/002 206/366 |
| 8,499,956 B2 * | 8/2013 | Westrate | .............. | B65D 5/3621 220/500 |
| 8,808,650 B1 * | 8/2014 | Iqbal | ........................ | B01L 9/06 422/562 |
| 9,096,349 B2 * | 8/2015 | Youell | ............... | B65D 5/48038 |
| D837,400 S * | 1/2019 | Evans | ........................ | D24/229 |
| 2002/0088723 A1 | 7/2002 | Lowry et al. | | |
| 2004/0118854 A1* | 6/2004 | Kutun | .................... | B65D 5/326 220/507 |
| 2007/0119740 A1* | 5/2007 | Clegg | ................... | A61M 5/008 206/366 |
| 2007/0172631 A1* | 7/2007 | Hugenholtz | ......... | B31D 5/0004 428/116 |
| 2008/0283535 A1* | 11/2008 | Westrate | .............. | B65D 5/3621 220/529 |
| 2010/0019024 A1 | 1/2010 | Wilms et al. | | |
| 2011/0297693 A1* | 12/2011 | Crabill | ................. | A47K 10/421 221/45 |
| 2013/0193196 A1* | 8/2013 | Hallam | ................ | B65D 5/0209 229/126 |
| 2013/0232917 A1* | 9/2013 | Duenas Sanchez | ...... | A61L 2/07 53/425 |
| 2017/0042356 A1* | 2/2017 | Hasani | ............... | B65D 81/3876 |
| 2018/0296298 A1* | 10/2018 | Escobar Fuertes | .. | A61B 50/362 |

\* cited by examiner

CARTRIDGE FOR MEDICAL AND HOSPITAL WASTE

OBJECT OF THE INVENTION

The present invention relates to a cartridge for medical and hospital waste which defines a cylindrical or prismatic container formed from cardboard sheets, closed at the bottom base and open at the top, the inside of which is divided into a plurality of cells into which medical waste products can be inserted or deposited, such as syringes, vials and other products which, in addition to having germs that are a source of disease and infections, can infect medical personnel through accidental cuts or pricks.

BACKGROUND OF THE INVENTION

Collecting medical and hospital waste to be subsequently treated and eliminated is problematic due to the aforementioned reasons. To protect medical personnel from accidentally coming into contact with the previously mentioned waste, there are different types of containers intended to collect waste, and in patent literature we can find several documents on this subject matter:

Document WO 2012056082 describes a cartridge for recycling medical waste which includes a body of recyclable material with a closed shape, the inner structure of which is divided into multiple compartments that define waste-receiving chambers, with axes that are parallel to one another and to the axis of the cartridge, said chambers closed at one end and open at the opposite end; the cartridge further comprising a heat-shrinkable plastic material which covers the cartridge at least on the sides. This invention further relates to a waste container which includes at least one waste-recycling cartridge of the type stated, as well as a method for compacting and sterilizing medical waste by using a recycling cartridge inserted in said waste container, inserting the recycling cartridge in a sterilization autoclave, with the aim of compressing the heat-shrinkable plastic material and forming a type of seal for the content in said recycling cartridge.

Document US 2010019024 describes a transport package to hold sample tubes and similar waste material that comprises a crush-resistant cardboard tube, with an absorbent lining that closes by means of end covers. One end this tube has a permanent closure and the other end can close by means of a cover that has an inner flange with a lip that couples the two sections of the tube.

Document US 2002088723 describes a shipping package for protecting a fragile item, such as a sample vial, which comprises a crush-resistant inner container and a tube formed from spirally wound fibrous plies adhered together, as well as an outer container surrounding the inner container. The outer container is a semi-rigid fluid-impervious can, while the inner container has a liner of absorbent material.

DESCRIPTION OF THE INVENTION

All of the known cartridges intended for collecting waste are generally rigid elements that even before being available to medical personnel take up the same amount of space as when they are in use, and therefore the distribution and storage thereof is quite complicated given that they are very voluminous.

This is partly due to the fact that they are divided on the inside by multiple partitions that define several chambers throughout the cartridge, which make up holes for depositing or inserting waste material, and to the fact that the entire assembly is crush-proof. In general, these cartridges define a tubular body made of recyclable material, of a cylindrical or prismatic configuration, closed at the bottom base and, optionally, are provided with a sealing lid, which also prevents the body of the container from being deformed and, therefore, occupies the same space the moment it is manufactured until it is used and recycled.

The cartridge of the invention is formed from a flexible sheet, such as cardboard, conveniently perforated, which defines the body and base of the cartridge.

Both the body and base of the cartridge, as well as the inner lattice, have characteristics that enable them to be compacted flat, minimizing the space needed for the storage and transport thereof and allowing the cartridge to be unfolded to form a cylindrical or prismatic body with holes inside for a position of use.

In the compacted position, the tubular body defines two superimposed side surfaces delimited by folding lines.

The base is formed by two semi-bases with a joined configuration according the perimeter of the cartridge, and which define two superimposed flaps fixed to one another, said flaps in the unfolded position of the cartridge forming a diametral partition that is in a line between the side surfaces of the body of the cartridge and slightly tucked below the base of the same, preventing the bottom of the cartridge from being deformed or crushed once it is unfolded.

These semi-bases are joined to the rectangles that will give shape to the cartridge by means of each flap, located in the central area of the cartridge in a folded position, which has a height equal to the aforementioned diametral partition in order for the base of the cartridge to be arranged tucked in at that height and to be supported by both elements, along with other peripheral supports defined by several tabs that radially emerge from the two semi-bases and are joined to them by means of folding lines.

The lattice that fills the body of the cartridge is made up of cardboard sheets and placed folded inside the cartridge, such that when the cartridge is unfolded it is opened to occupy the entire inner surface of the tubular body.

This lattice has a honeycomb-type configuration and is preferably fixed inside the tubular body of the cartridge at two diametrically opposite points located at right angles with respect to the side folding lines of the same.

In one embodiment of the invention, the base is hard cardboard, and the semi-bases constituting the same are made up of hard cardboard, or are made from papier-mâché.

DESCRIPTION OF THE FIGURES

As a complement to the description being made, and for the purpose of helping to make the characteristics of the invention more readily understandable, this specification is accompanied by a set of drawings which, by way of illustration and not limitation, represent the following.

PREFERRED EMBODIMENT OF THE INVENTION

The cartridge for medical and hospital waste of the invention has a tubular body (1) made of recyclable material in the figure of a cylindrical configuration, although, it could perfectly well be represented prismatically with an octogonal or decagonal base, which is closed at the lower base thereof by a base (3), while the upper end is open, although it may receive a lid that couples to the outside or inside. On the inside the container is divided into multiple partitions that form a lattice (2) which defines several chambers throughout the cartridge forming holes for depositing or inserting waste material.

In one embodiment of the invention, said chambers or holes have a square shape.

Figure 3:
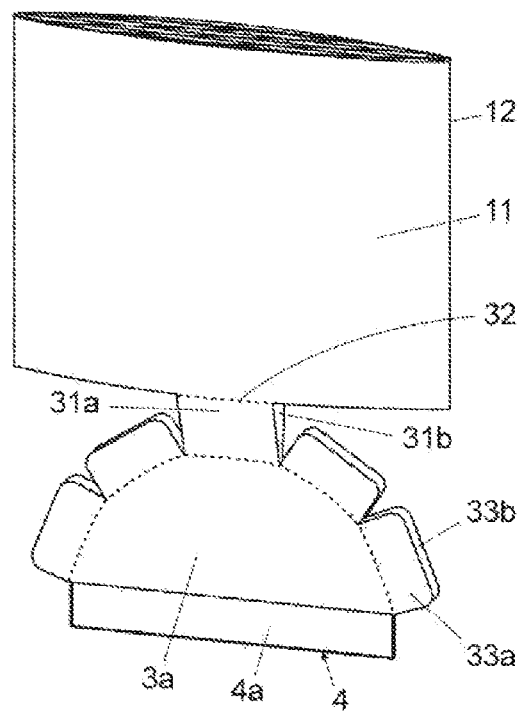
FIGS. 3, 4 and 5 show front, side and upper plan views, respectively, of the previous cartridge in a compacted position, just as it would be stored and distributed before being unfolded for use.
Figure 4:
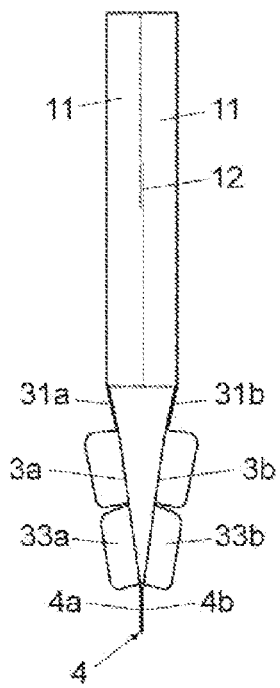
Figure 5:
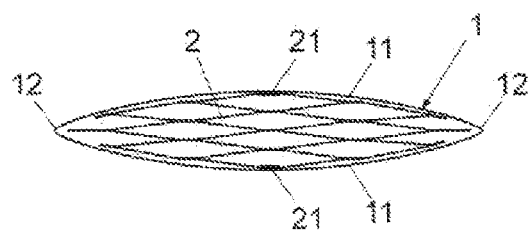

This cartridge is structured by a flexible sheet, conveniently cut, which defines both the tubular body (1) and the base (3) of the same. This sheet is folded onto itself at the middle of the base (3) and by folding lines (12) of the tubular body of the cartridge, forming an easy to store flat body, occupying a minimum amount of space, as shown in FIGS. 3 and 4.

In the cut sheet, side surfaces (11) stick out which, when unfolded or separated, hollowing out the inner space, define the walls of the tubular body (1) of the cartridge. These surfaces are delimited by the folding lines (12) of the tubular body (1), or any other conventional means.

Each one of these side surfaces (11) is extended downward and through the center by a flap (31a, 31b) joined to the same by means of a folding line (32).

Said flaps are extended to both semi-bases (3a, 3b) which together define a configuration according to the perimeter of the cartridge (1) once it is enabled for use.

These semi-bases (3a, 3b) are joined together on the outside by means of superimposed flaps (4a, 4b) that make up a diametral partition (4) when the cartridge is in a position of use.

The semi-bases (3a, 3b) are further provided with several foldable tabs (33) that radially emerge from the same.

Figure 1:
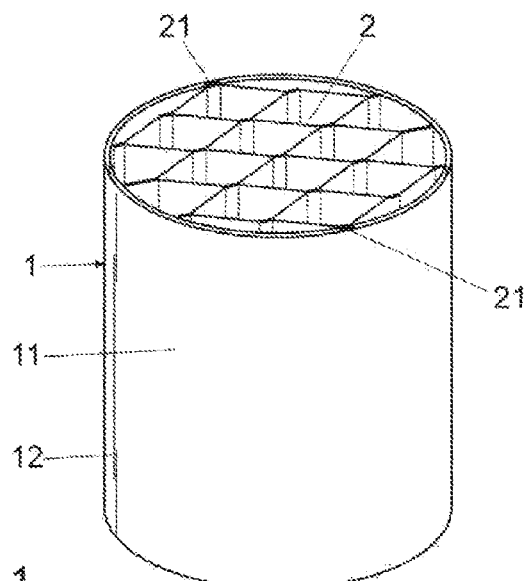
FIGS. 1 and 2 represent perspective views from an upper and lower point of view, respectively, of the cartridge of the present invention in a position of use.
Figure 2:
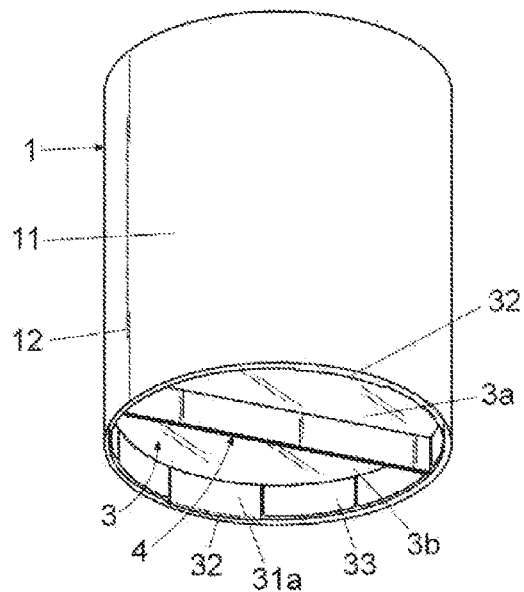

Inside the tubular body, the cartridge has a lattice (2) that delimits the cells containing the waste that is deposited in the same. FIG. 1 shows that this lattice is fixed to the tubular body (1) at two diametrically opposite points (21), located at right angles with respect to the folding lines (12) of the tubular body, thus, when enabling the cartridge for use and providing it with its round shape, the lattice (2) stretches and the inner partitions take the position shown in FIG. 1, wherein they are straight and aligned and the lattice defines a honeycomb-type configuration.

As can be seen in FIG. 3, the cartridge, in the position for storage and distribution, forms a flat body, which may be easily included in boxes, since it occupies hardly any volume in relation to when it is unfolded and in a position of use.

When the cartridge is going to be used, all one needs to do is simply unfold the two side surfaces (11) and bend the base (3) toward the inside of the tubular body (1) such that the two semi-bases (3a, 3b) are coplanar.

Being bent inwards, the base fits inside the tubular body (1), the two semi-bases (3a, 3b) remaining on the same plane, slightly penetrating inside the cartridge, separated by the diametral partition (4) and the flaps (31a, 31b) folded inside, while the tabs (33) are folded towards the outside and in contact with the side surfaces (11).

Since the diametral partition (4), the flaps (31a, 31b) and the tabs (33) have the same height, they, together with the rim of the cartridge, make up several supports for the base (3) which prevent the bottom of the cartridge from dropping out when the cartridge is carrying a load.

In one embodiment of the invention, the base (3) made up of hard cardboard, or of papier-mâché.

The invention claimed is:

1. A cartridge for medical and hospital waste comprising:
    a tubular flexible body (1) having a top portion, a bottom portion and side surfaces (11), wherein the side surfaces (11) of said tubular body (1) define an inner space and walls of the tubular body (1) of a cartridge when unfolded or separated;
    a base (3) comprising semi-bases (3a, 3b) having an upper edge and a lower edge, wherein the tubular flexible body (1) and the base (3) are connected via flaps (31a, 31b) that are connected between a center area of the upper edge of said semi-bases (3a, 3b) and a center area of said bottom portion of the flexible body (1) by way of folding lines;
    a plurality of foldable tabs (33) connected to the upper edge of said semi-bases (3a, 3b) by way of folding lines, said plurality of foldable tabs (33) being provided at both sides of said flaps (31a, 31b) and extending along the entire length of said upper edge of the semi-bases (3a, 3b);
    a diametral partition (4) extending away from the lower edge of said semi-bases (3a, 3b) and extending along the entire length of said lower edge; and
    a lattice of sheets (2) provided inside the inner space defined by said side surfaces (11).

2. The cartridge of claim 1, wherein said lattice (2) is fixed to said side surfaces (11) at two diametrically opposite positions (21) inside the inner space.

3. The cartridge of claim 1, wherein the flaps, the plurality of foldable tabs and the diametral partition have the same height so that together with the inner peripheral rim of the container form a uniform support for the base (3) when the cartridge is unfolded.

4. The cartridge of claim 1, wherein the lattice of sheets is situated folded inside the tubular body (1) and occupies the entire inner space when the cartridge is unfolded.

5. The cartridge of claim 1, wherein the lattice of sheets defines several chambers or holes with a square shape for depositing or inserting waste material.

6. The cartridge of claim 1, wherein the base (3) is made of hard cardboard or papier-mâché.

* * * * *